United States Patent
Aizawa et al.

(10) Patent No.: US 10,234,665 B2
(45) Date of Patent: Mar. 19, 2019

(54) INFRARED MICROSCOPE

(71) Applicant: JASCO Corporation, Tokyo (JP)

(72) Inventors: Kento Aizawa, Tokyo (JP); Hiroshi Sugiyama, Tokyo (JP); Jun Koshobu, Tokyo (JP)

(73) Assignee: JASCO Corporation, Tokyo (JP)

( * ) Notice: Subject to any disclaimer, the term of this patent is extended or adjusted under 35 U.S.C. 154(b) by 0 days.

(21) Appl. No.: 15/954,679

(22) Filed: Apr. 17, 2018

(65) Prior Publication Data

US 2018/0307018 A1 Oct. 25, 2018

(30) Foreign Application Priority Data

Apr. 19, 2017 (JP) .................. 2017-082515

(51) Int. Cl.
*G02B 21/00* (2006.01)
*G01N 21/35* (2014.01)

(52) U.S. Cl.
CPC ......... *G02B 21/0032* (2013.01); *G01N 21/35* (2013.01); *G02B 21/006* (2013.01); *G02B 21/0048* (2013.01)

(58) Field of Classification Search
CPC ................ G01N 21/35; G02B 21/0032; G02B 21/0048; G02B 21/006
See application file for complete search history.

(56) References Cited

U.S. PATENT DOCUMENTS

| | | | | |
|---|---|---|---|---|
| 4,253,022 A * | 2/1981 | Allen | ................. | G01J 5/061 250/349 |
| 4,446,372 A * | 5/1984 | Gurnee | ............. | H01L 31/02164 250/334 |
| 5,282,473 A * | 2/1994 | Braig | ................. | A61B 5/083 250/343 |
| 2002/0033452 A1 | 3/2002 | Hoult | | |
| 2008/0049304 A1* | 2/2008 | Deck | .................. | G01J 3/02 359/350 |
| 2015/0346082 A1* | 12/2015 | Mao | .................. | G01N 21/59 250/564 |

(Continued)

FOREIGN PATENT DOCUMENTS

JP 2002188958 A 7/2002

*Primary Examiner* — Marcus H Taningco
(74) *Attorney, Agent, or Firm* — Rankin, Hill & Clark LLP

(57) ABSTRACT

The problem to be solved by the present invention is to provide an infrared microscope with good measuring accuracy and less crosstalk.

The infrared microscope 10 comprises a light source 12, an irradiating unit 14 for irradiating the infrared light from the light source to a sample 16, a focusing unit 18 for focusing the infrared light transmitted through or reflected by the sample 16, and a detector 20 for detecting the focused infrared light. The irradiating unit 14 comprises a first aperture 24, and the first aperture is disposed at a position where the infrared light from the light source passes therethrough. The focusing unit 18 comprises a second aperture 30, and the second aperture is disposed at an imaging position of the infrared light at the first aperture 24. The first aperture has a plurality of holes, and the holes are disposed at intervals corresponding to the arrangement of the light-receiving elements provided in the detector 20 to detect the infrared light as a detecting light. The second aperture 30 has holes that have the same size and arrangement as the first aperture 24.

24 Claims, 6 Drawing Sheets

(56) References Cited

U.S. PATENT DOCUMENTS

| | | | | |
|---|---|---|---|---|
| 2016/0187202 A1* | 6/2016 | Miller | ....................... | G01J 5/10 |
| | | | | 250/338.1 |
| 2018/0180642 A1* | 6/2018 | Shetty | ................... | G01Q 30/025 |
| 2018/0191967 A1* | 7/2018 | Kester | ....................... | G01J 3/02 |

\* cited by examiner (a)   (b)   (c)

(a)　　(b)　　　　(c)

INFRARED MICROSCOPE

RELATED APPLICATIONS

This application claims the priority of Japanese Patent Application No. 2017-82515 filed on Apr. 19, 2017, the disclosure of which is incorporated herein by reference in its entirety.

FIELD OF THE INVENTION

The present invention relates to infrared microscopes, and particularly to improvements in apertures in infrared microscopes for obtaining high spatial resolution.

BACKGROUND OF THE INVENTION

Conventionally, infrared microscopes as means for obtaining optical information of microscopic parts on samples are known. For example, to investigate molecular structures of organic substances attached to a surface of an individual, infrared microscopes irradiate infrared light to a microscopic part on a sample held by a stage and detect transmitted or reflected infrared light by a detector to measure absorption spectrum and the like.

Recently, measurement methods which irradiate linear infrared light to a sample (linear irradiation) to obtain spectra of a plurality of points from the elongated irradiated region are used. These methods shorten measurement time compared to measurement methods which uses general spot irradiation. In measurement performed by linear irradiation, generally, an array detector is used to detect spectra of a plurality of point. However, crosstalk, which spectra overlap each other, cannot be avoided, and sufficient spatial resolution cannot be obtained. Patent Literature 1 discloses an art to eliminate crosstalk (overlapping of spectra) by irradiating a linear infrared light to a sample and making spaces bigger between light-receiving elements in a light-receiving element surface of a detector for detecting the infrared light transmitted through or effected by the sample.

CITATION LIST

Patent Literature

PATENT LITERATURE 1: Japanese Patent Publication No. JP2002-188958

DISCLOSURE OF THE INVENTION

Problem to be Solved by the Invention

As described above, crosstalk can be avoided, in short-wavelength light by making spaces between light-receiving elements of the detector bigger. However, crosstalk cannot be eliminated completely in king-wavelength light. Particularly, in infrared microscopes, a long-wavelength region is a wavelength region referred to as a fingerprint region which is important for identifying substances, and accurate measurement is prevented due to effects of crosstalk in this region. In addition, since elements are spaced apart in short-wavelength light, optical information of the sample surface may be partially missing. Therefore, there is still more space for improvement for accurate measurement.

Means to Solve the Problem

The present invention has been made in view of the problems of the prior art, and the object is to provide an infrared microscope capable of measurement with good accuracy and less crosstalk.

To solve the above-described problems, the infrared microscope of the present invention comprises:

a light source for irradiating an infrared light, an infrared light irradiating unit for irradiating the infrared light to a sample, an infrared light focusing unit for focusing the infrared light transmitted through or reflected by the sample, and a detector for detecting the focused infrared light, wherein the infrared light irradiating unit comprises a first aperture, and the first aperture is disposed at a position which the infrared light from the light source passes to be irradiated to the sample;

the infrared light focusing unit comprises a second aperture, and the second aperture is disposed at an imaging point of the infrared light at the first aperture;

the first aperture has a plurality of holes;

the holes are disposed with intervals which correspond to an arrangement of light-receiving elements disposed in the detector, so that the detector can detect the infrared light as a detecting light; and the second aperture has holes having the same size and arrangement as the first aperture.

Further, the first and the second aperture are preferably provided in pluralities having different number of holes or different arrangements, and are selected in accordance with a wavelength of the infrared light.

Further, the first and the second aperture preferably has a plurality of holes disposed with regular intervals in one direction.

Further, the holes of the first and the second aperture are preferably two-dimensionally disposed with regular intervals in a first and a second arrangement direction.

Further, the first and the second aperture preferably has a plurality of holes disposed with irregular intervals in one direction.

Further, the holes of the first and the second aperture are preferably two-dimensionally disposed with irregular intervals in a first and a second arrangement direction.

Further, both or either one of the infrared light irradiating unit and the infrared light focusing unit for focusing the infrared light transmitted through the sample preferably comprises a Cassegrain mirror.

Further, the infrared light irradiating unit and the infrared light focusing unit for focusing the infrared light transmitted through the sample preferably uses the same Cassegrain mirror.

Further, the detector is a MCT detector, wherein the aperture is switched in accordance with the arrangement of the light-receiving elements in the MCT detector and the wavelength of the infrared light.

Further, the infrared light irradiating unit preferably comprises an interferometer for producing an interference wave from the infrared light irradiated from the light source in accordance with scanning of a moving mirror, and an analyzer for analyzing the interference wave of the infrared light detected by the detector is preferably provided.

Further, the first aperture is preferably included in the interferometer.

Further, the infrared light irradiating unit comprises a first irradiation path for measurement by transmission and a second irradiation path for measurement by reflection, and both of the first and the second irradiation path comprise the first aperture.

Further, the wavelength of the infrared light is preferably 2 μm or more.

Effect of the Invention

According to the infrared microscope of the present invention, disposing the first aperture having a plurality of holes between the light source and the sample, and disposing the second aperture corresponding to the first aperture between the sample and the detector (disposing the second aperture at an imaging point of the infrared light at the first aperture) enable the holes to obtain confocal effect simultaneously, and measurement with good accuracy and less crosstalk becomes possible. Further, a plurality of the first and the second aperture is provided, respectively, so that a suitable aperture can be selected in accordance with the sample to be measured and the wavelength the infrared light for measurement. For example, a conventional aperture can be used when the wavelength of the infrared light is short, and an aperture having plurality of holes can be used when the wavelength of the infrared light is long for reducing crosstalk.

BEST MODE FOR CARRYING OUT THE INVENTION

Hereinbelow, the infrared microscopes of the present invention are described with reference to the figures, but are not limited to the examples described below as long as the aim of the present invention is not exceeded.

The First Embodiment

Figure 1:
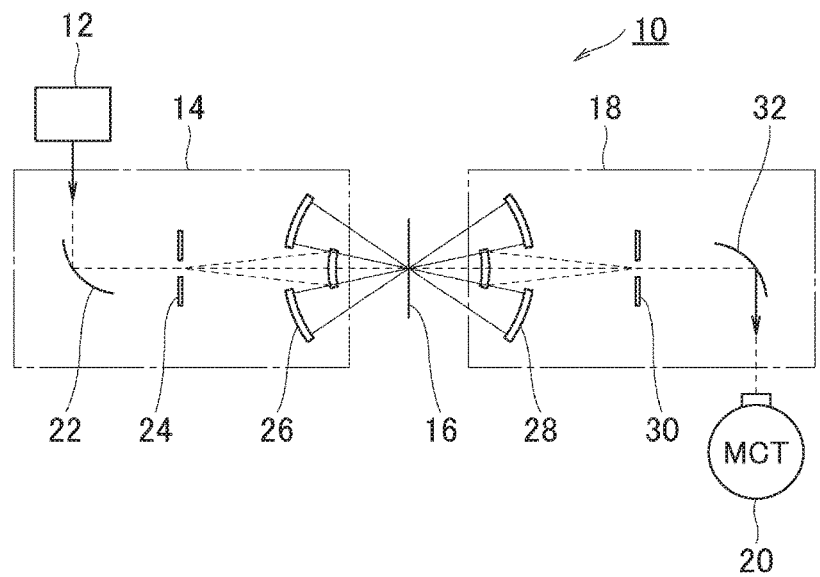
FIG. 1 shows a schematic configuration of a first embodiment of the infrared microscope according to the present invention.

FIG. 1 is a schematic diagram of the infrared microscope according to the first embodiment of the present invention. It is a simplified schematic configuration, so that explanation of the present embodiment becomes easier. Therefore, although it is not shown in FIG. 1, configuration components which are necessary for general microscopes such as a movable stage for placing the sample, a computer for analyzing, the detection light, and the like are comprised. The infrared microscope 10 shown in FIG. 1 comprises a light source 12 for irradiating an infrared light, an infrared light irradiating optical system 14 for irradiating the emitted infrared light to a sample 16, an infrared light focusing optical system 18 for focusing the infrared light transmitted through the sample 16, and a MCI detector 20 for detecting the focused infrared light.

Characteristic features of the present invention are that the infrared light irradiating optical system 14 comprises a first aperture 24 having at least one or more holes, the infrared focusing optical system 18 comprises a second aperture 30 of which the position and the size of the holes correspond to the first aperture 24, and the second aperture 30 is disposed at an imaging point of the infrared light at the first aperture 24. Therefore, as shown in FIG. 1, the first aperture 24 is disposed between the light source 12 and the sample 16, and the second aperture 30 is disposed between the sample 16 and the detector 20.

First of all, the infrared light irradiating optical system 14 and the irradiation process of the infrared light are described in detail.

The infrared light irradiating optical system 14 comprises an irradiating mirror 22 for reflecting the infrared light toward the sample 16, the first aperture 24, and an irradiating Cassegrain mirror 26 for irradiating the infrared light to the sample 16 as a beam-spot. The infrared light emitted from the light source 12 reaches the irradiating mirror 22 to be reflected toward the sample 16. The wavelength of the infrared light here depends on the sample to be measured and the measuring method (the wavelength of the infrared light, measurement by transmission or reflection, and the like), but it is preferably 1.0 to 30 μm, and more preferably 2.0 to 25 μm. Then, the infrared light reflected by the reflecting mirror 22 reaches the first aperture 24.

Hereinbelow, the shape of the first aperture 24 is described.

Figure 2:
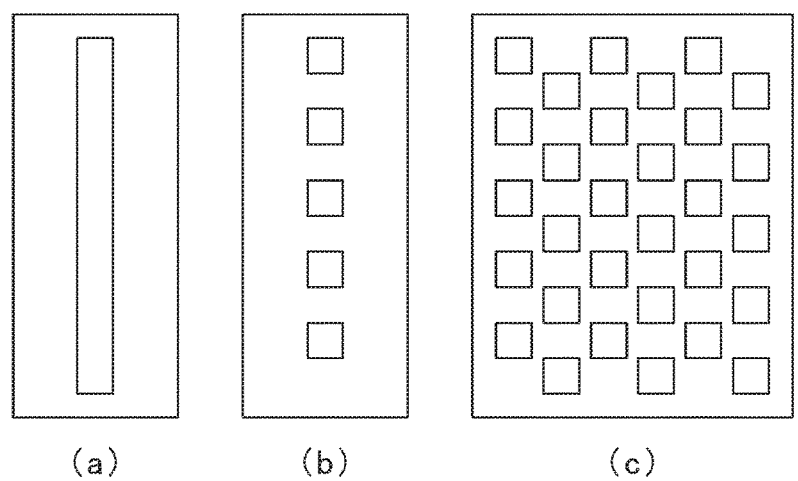
FIG. 2 shows the shapes of the first and the second aperture used in the first embodiment of the infrared microscope according to the present invention.

FIGS. 2 (a) to (c) show external shapes of the aperture 24 and shapes of the holes. The first aperture 24 has at least one or more holes, and each hole acts as general apertures (pinholes). Further, the first aperture 24 is not provided only in one kind, but in several kinds, such as one having one elongated hole as shown in FIG. 2 (a), one having a plurality of holes disposed with predetermined intervals in a vertical direction as shown in FIG. 2 (b), one having a plurality of holes two-dimensionally disposed with predetermined intervals in a vertical and a horizontal directions as shown in FIG. 2 (c), and the like. Three kinds of apertures are provided in the present embodiment, but it can be two kinds, or more than three kinds. Further, in infrared microscopes dedicated to measure specific samples, the first aperture 24 may be one kind having at least one or more holes. Although holes are regularly disposed in FIGS. 2 (a) to (c), the present invention is not limited to such arrangements. For example, an aperture having holes disposed irregularly, or in other arrangements may be used. In addition, the external shape of the aperture is not limited to square shapes as shown in FIGS. 2 (a) to (c), and may be a circular shape, or other shapes. Among the first apertures 24 which are provided in a plurality of kinds, a suitable aperture is selected in accordance with characteristics of the sample 16 and the wavelength of the infrared light for measurement. In the present embodiment, the aperture shown in FIG. 2 (b) is selected.

Figure 3:
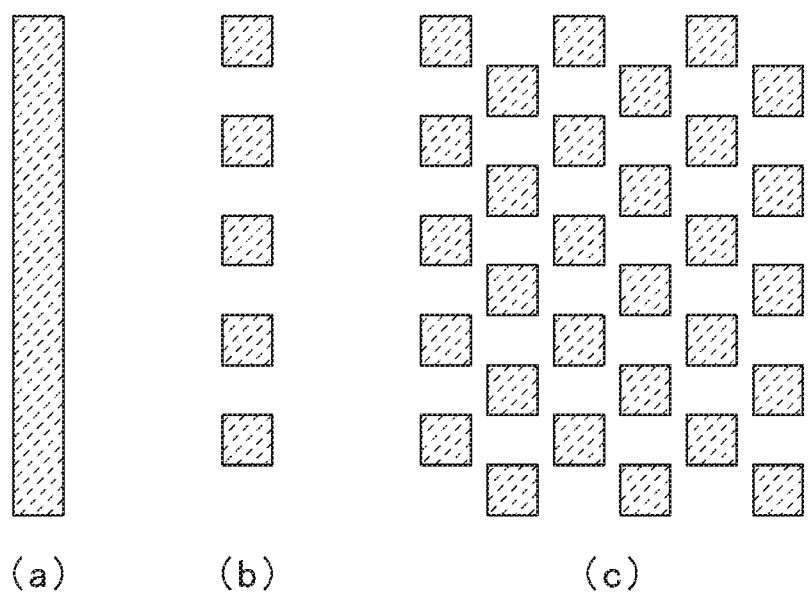
FIG. 3 shows the shapes of beam-spots on the sample surface in the first embodiment of the infrared microscope according to the present invention.

The shape of the infrared light is changed by the selected first aperture 24 (FIG. 2 (b)), and the infrared light forms beam-spots by the irradiating Cassegrain mirror 26 to be irradiated toward the sample 16. The infrared light irradiated toward the sample 16 forms beam-spots in a shape shown in FIG. 3 (b) on the surface of the sample 16. Further, when the aperture shown in FIG. 2 (a) is selected, the shape of the beam-spot on the surface of the sample 16 will be a shape shown in FIG. 3 (a). When the aperture shown in FIG. 2 (c) is selected, the shape of the beam-spots on the surface of the sample 16 will be a shape shown in FIG. 3 (c). The infrared light as a beam-spot transmits through the sample 16 in the shape of FIG. 3 (b), and proceeds to the infrared light focusing optical system 18.

Next, the infrared light focusing optical system 18 is described in detail.

The infrared light focusing optical system 18 comprises a focusing Cassegrain mirror 28 for focusing the infrared light transmitted through the sample 16 as beam-spots, the second aperture 30 corresponding to the first aperture 24, and a focusing mirror 32 for reflecting the light passed through the second aperture toward the MCT detector 20. The infrared light transmitted through the sample 16 in the shape shown FIG. 3 (b) is focused by the focusing Cassegrain mirror 28, and reaches the second aperture 30.

Hereinbelow, the second aperture 30 is described.

The second aperture 30 is equivalent to the first aperture 24. "Equivalent" as used herein means that aperture functions (pin-hole function) such as the position and the size of the holes are equivalent. Therefore, for example, as long as the position and the size of the holes are the same as shown in FIGS. 2 (a) to (c), external dimension, material, color, shape, and the like of the aperture itself may be different. For example, although the first aperture 24 is square-shaped in FIG. 2, the second aperture 30 may be circular or in other shape. The second aperture 30 is disposed at the imaging point of the infrared light at the first aperture 24. Since it is sufficient if the second aperture 30 obtains confocal effect of the infrared light at the first aperture 24, the second aperture 30 can be disposed at a position slightly shifted from the imaging position, for example, as long as it is in a similar relationship with the first aperture 24 to obtain confocal effect.

In the present embodiment, since the first apertures 24 are provided in three kinds, the second apertures 30 are provided in three kinds to correspond to the first apertures 24. The second aperture 30, which correspond to the preselected first aperture 24 and has equivalent aperture functions, is selected. The second aperture 30 equivalent to the first aperture 24 is disposed between the sample 16 and the MCI detector 20 in the infrared light focusing optical system 18, so that each hole obtains confocal effect simultaneously, and a good infrared light can be focused. The aperture shown in FIG. 2 (b) is selected in the present embodiment, so that confocal effect can be obtained simultaneously for all holes disposed with predetermined intervals in vertical direction. As a result, spatial resolution for a plurality of holes can be improved simultaneously. Further, in measuring different samples, the aperture having a plurality of holes as shown in FIG. 2 (b) can be switched to the aperture having a elongated slit (FIG. 2 (a)) when measuring with short wavelength infrared light. Similarly, it can be switched to the aperture having holes disposed regularly in two-dimensional direction (FIG. 2 (c)) when two dimensional directions of the sample are to be measured simultaneously.

The infrared light passed through the second aperture 30 is then reflected toward the MCT detector 20 by the focusing mirror 32, and is guided to the MCT detector 20 as a good infrared light, so that measurement with good accuracy may be performed.

Figure 4:
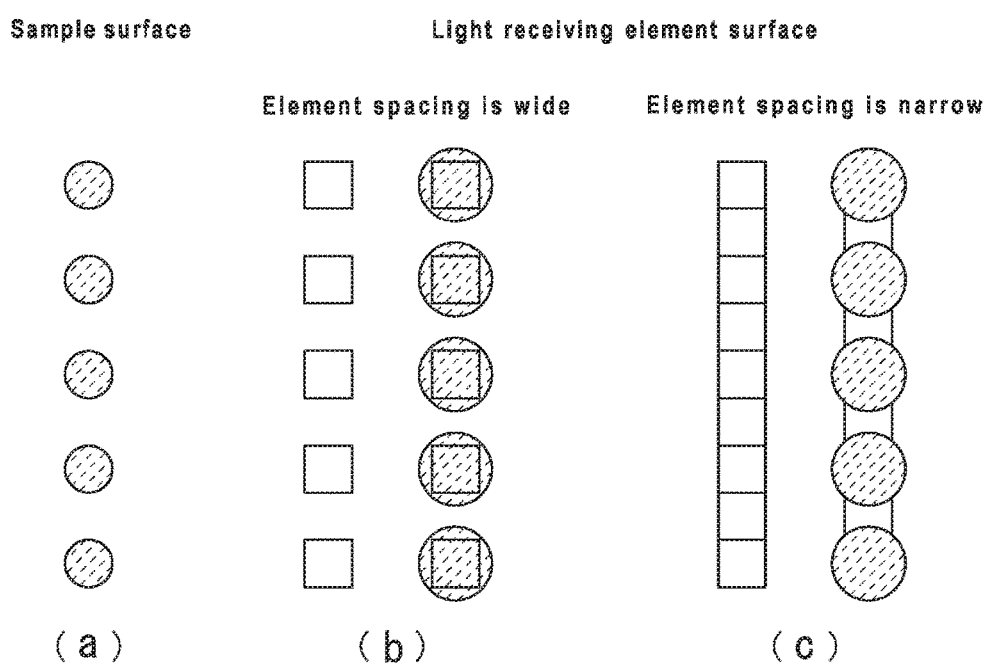
FIG. 4 shows relationship of the light-receiving elements and detection lights of the detector in the first embodiment of the infrared microscope according to the present invention.

The detecting light-receiving element faces of the MCT detector 20 in the present embodiment are shown in FIGS. 4 (a) to (c). In FIG. 4, the infrared lights are shown in circular-shape to clearly distinguish from the light-receiving elements on the light-receiving element face, although the infrared lights are in the same shape as the holes of the aperture on the actual light-receiving element face. FIG. 4 (a) shows shapes of the beam-spots on the sample face. As described above, the first and the second aperture having shapes shown in FIG. 2 (b) are used in the present embodiment. Thus, the detected infrared light is in spots with predetermined intervals in vertical direction. The infrared light is guided to the MCT detector 20 while maintaining the shape shown in FIG. 4 (a). Therefore, when elements are disposed with intervals on the light-receiving element face of the MCT detector 20, for example, crosstalk on the light-receiving element face can be prevented as shown in FIG. 4 (b). More accurate measurement is possible by preventing crosstalk of infrared spectra of 400 cm$^{-1}$ to 4,000 cm$^{-1}$ (wavelength of 2.5 μm to 25 μm), which is the fingerprint region that is very important for identifying substances. In addition, when intervals between the elements are narrow as shown in FIG. 4 (c), crosstalk can be ignored if the elements in between are ignored. Thus, measurement with less crosstalk becomes possible.

By using the first aperture 24 having a plurality of holes and the second aperture 30 corresponding to the first aperture 24, confocal effect can be obtained in a plurality of points simultaneously, and accurate measurement with less crosstalk becomes possible.

The Second Embodiment

Next, an infrared microscope according to the second embodiment of the present invention is described in detail with reference to figures. Configurations in common with the infrared microscope 10 of the first embodiment shown in FIG. 1 are represented with reference numbers of which 100 are added respectively.

Figure 5:
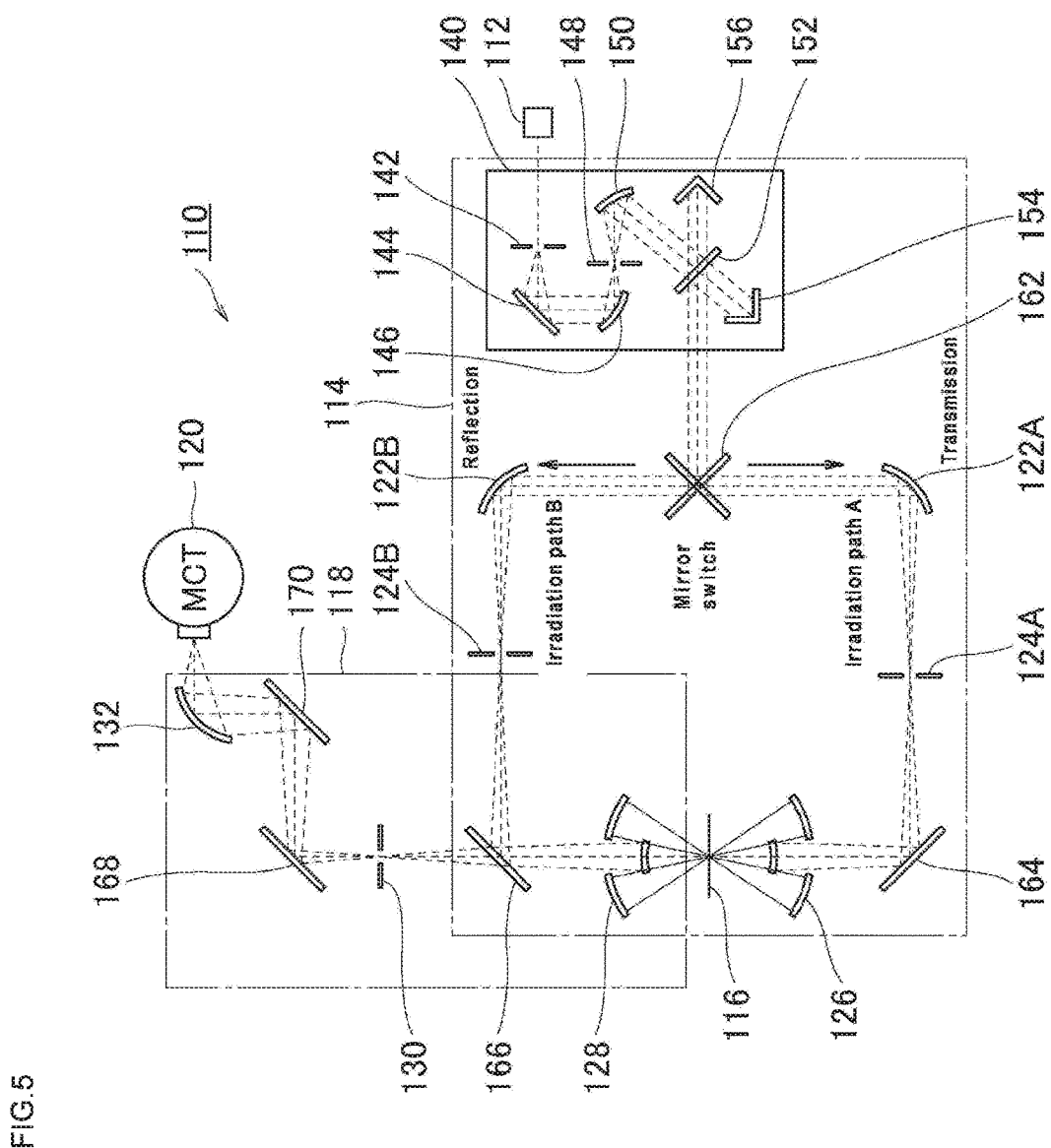
FIG. 5 shows a schematic configuration of a second embodiment of the infrared microscope according to the present invention.

FIG. 5 is a schematic diagram of the infrared microscope according to the second embodiment of the present invention. The infrared microscope 110 shown in FIG. 5 comprises a light source 112 for irradiating an infrared light, an infrared light irradiating optical system 114 for irradiating the emitted infrared light to a sample 116, an infrared light focusing optical system 118 for focusing the infrared light transmitted through or reflected by the sample 116, and a MCT detector 120 for detecting the focused infrared light.

The present embodiment is an embodiment which uses the present invention to a Fourier transform infrared spectrometer (FTIR). The FTIR irradiates an infrared light to the sample 116 by using an interferometer 140 comprised to the infrared light irradiating optical system 114, detects the infrared light transmitted through or reflected by the sample 116, and performs Fourier transformation by a computer, and the like to calculate and analyze each wavelength component. The first apertures 124 (not shown as 124 in the figure, but it means both of 124A and 124B herein) are disposed respectively in an irradiation path A for irradiating the infrared light to the sample 116 for transmission measurement, and in an irradiation path B for irradiating the infrared light to the sample 116 for reflection measurement. In addition, a switching mirror 162 for guiding the infrared light to either one of the irradiation path A or B is comprised.

First of all, the infrared light irradiating optical system 114 and the irradiation process of the infrared light are describe in detail.

The infrared light irradiating optical system 114 comprises: an interferometer 140; a switching mirror 162 for reflecting the infrared light to either one of an irradiation path A or B; irradiating mirrors 122A and 122B for guiding the infrared light toward the sample 116; a transmitted light guiding mirror 164 for guiding the infrared light which travels the irradiation path A (the infrared light which transmits through the sample) toward the sample 116; a reflected light guiding mirror 166 for guiding the infrared light which travels the irradiation path B (the infrared light which is reflected by the sample) toward the sample 116; an irradiating Cassegrain mirror 126 for irradiating the infrared light for transmission measurement; and a focusing Cassegrain mirror 128 for irradiating the infrared light for reflection measurement. The infrared light emitted from the light source 112 becomes an interference wave by the interferometer 140, which will be described below, and proceeds toward the switching mirror 162.

Hereinbelow, the interferometer 140 is described. The interferometer 140 comprises: an interferometer slit 142; a first interferometer mirror 144; a second interferometer mirror 146; a resolution determining slit 148 for determining wavenumber resolution of the interferometer 140; a third interferometer mirror 150; a semi-transparent mirror 152 for transmitting approximately half of the infrared light among the infrared light reflected by the third interferometer mirror 150 and reflecting the other half; a fixed mirror 154 in a corner cube shape for reflecting the infrared light to the irradiated direction; and a moving mirror 156 also in a corner cube shape which reflects the infrared light to the irradiated direction and moves to change the distance between the semi-transparent mirror 152.

The infrared light emitted from the light source 112 is guided to the interferometer 140, passes through the interferometer slit 142, changes its direction by the first interferometer mirror 144 and the second interferometer mirror 146, passes through the resolution determining slit 148, and reaches the third interferometer mirror 150. Then, the infrared light is reflected toward the semi-transparent mirror 152 by the third interferometer mirror 150 to be irradiated to the semi-transparent mirror 152. Here, the infrared light is divided into two, such that a half of the infrared light becomes a transmitted light and the other half becomes a reflected light. The two infrared lights proceed toward the fixed mirror 154 and the moving mirror 156 to be reflected thereby. The two infrared lights come back to the semi-transparent mirror 152, and are synthesized again to become an interference light. That is, the interference wave from two different infrared lights can be obtained by changing the position of the moving mirror 156 (optical path difference).

The obtained infrared light as the interference light is guided to the irradiation path A for transmission measurement or the irradiation path B for reflection measurement by the switching mirror 162. For example, when the sample 116 is to be measured by the infrared light transmitted through the sample 116, the infrared light travels the irradiation path A to be irradiated to the sample 116 by the transmitted light guiding mirror 164. When the sample 116 is to be measured by the infrared light reflected by the sample 116, the infrared light travels the irradiation path B to be reflected toward the sample 116 by the reflected light guiding mirror 166. Further, both of the irradiation paths A and B comprise incident mirrors 122 (122A in the irradiation path A, and 122B in the irradiation path B), and first apertures 124 (124A in the irradiation path A, and 124B in the irradiation path B). Both of the irradiation paths A and B have same configurations, so that one infrared microscope 110 can handle different measurement methods such as measurement by transmission or reflection.

Next, the infrared light focusing optical system 118 shown in FIG. 5 is described.

The infrared light focusing optical system 118 comprises: a focusing Cassegrain mirror 128 for focusing the infrared light transmitted through or reflected by the sample 116; a second aperture 130 corresponding to the first aperture 124; a first plane mirror 168 and a second plane mirror 170 for guiding the infrared light which passed the second aperture; and a focusing mirror 132 for reflecting the focused infrared light toward the MCT detector 120. The focusing Cassegrain mirror 128 described here is the same as the focusing Cassegrain mirror 128 for irradiating the infrared light which traveled the irradiation path B in the infrared light irradiating optical system 114 to the sample 116.

The infrared light transmitted through or reflected by the sample 116 is focused by the focusing Cassegrain mirror 128. Then the focused infrared light is transmitted through the reflected light guiding mirror 166, and reaches the second aperture 130. The second aperture 130 in the present embodiment is the same as the aperture described in the first embodiment (FIG. 2 (b)), and corresponds to the first aperture 124.

The infrared light which passed the second aperture 130 is reflected toward the focusing mirror 132 by the first plane mirror 168 and the second plane mirror 170. Then, the infrared light is reflected to the MCT detector 120 by the focusing mirror 132 to be guided to the MCT detector 120 as a good infrared light for measurement.

In the present embodiment, both of the irradiation paths A and B in the infrared light irradiating optical system 114 comprise the first apertures 124 (124A in the irradiation path A, and 124B in the irradiation path B) respectively and the infrared light focusing optical system 118 comprises the second aperture 130 which corresponds to the first aperture 124. Therefore, measurement by transmission and reflection can be performed in one microscope, and a good measurement with confocal effect obtained by the first and the second aperture and less crosstalk becomes possible.

Third Embodiment

Next, an infrared microscope according to a third embodiment of the present invention is described with reference to the figures. Configurations in common with the infrared microscope 110 of the second embodiment shown in FIG. 5 are represented with reference numbers of which 100 are added respectively.

Figure 6:
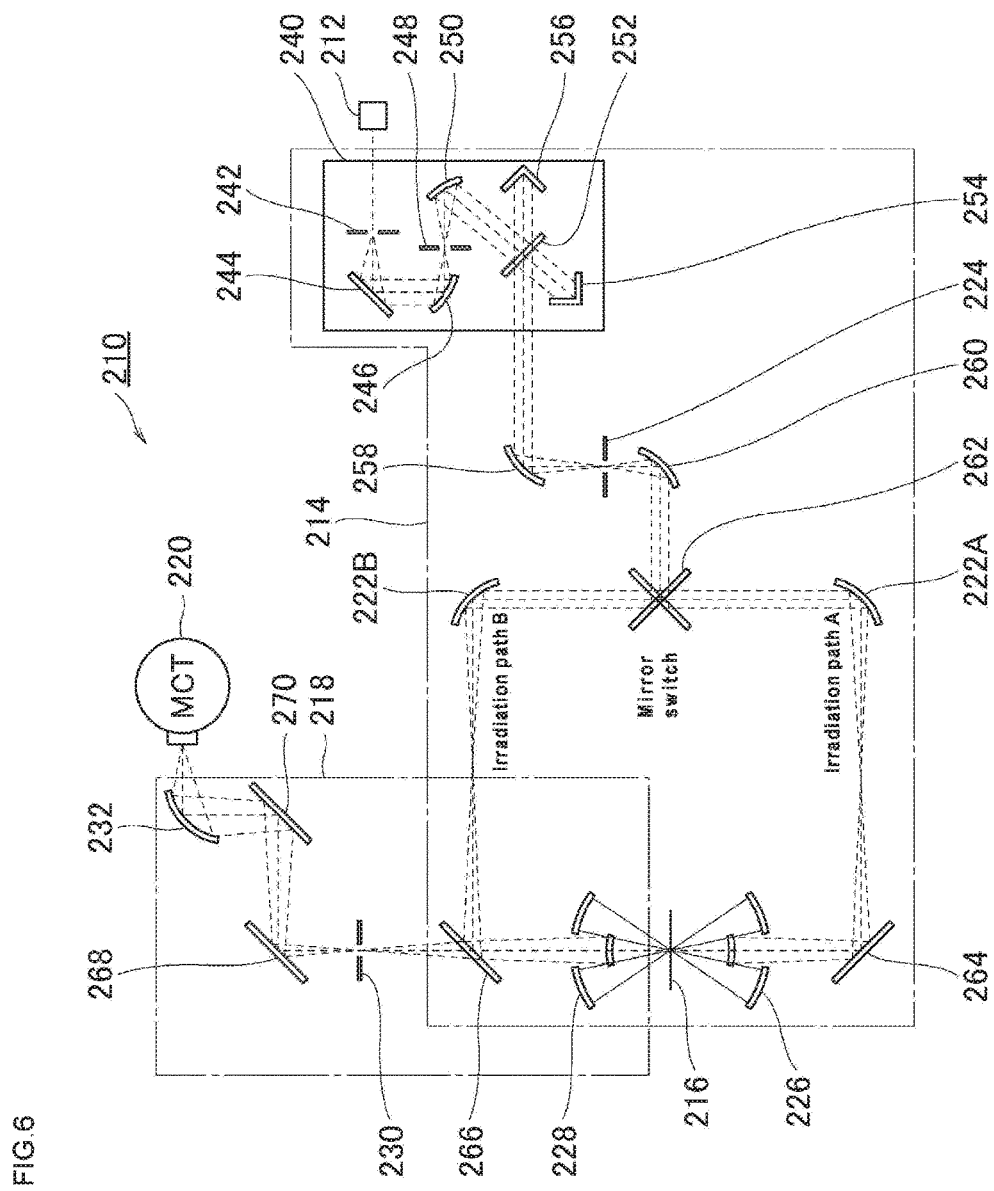
FIG. 6 shows a schematic configuration of a third embodiment of the infrared microscope according to the present invention.

FIG. 6 is a schematic diagram of the infrared microscope according to the third embodiment of the present invention. The infrared microscope 210 shown in FIG. 6 comprises: a light source 212 for emitting an infrared light; an infrared light irradiating optical system 214 for irradiating the emitted infrared light to a sample 216; an infrared light focusing optical system 218 for focusing the infrared light transmitted through or reflected by the sample 216; and a MCT detector 220 for detecting the focused infrared light. The present embodiment is also an embodiment that uses the present invention to a similar FTIR like the second embodiment.

A characteristic feature of the present embodiment is that the first aperture 224 is not provided in the irradiation paths A and B, but is provided between the interferometer 240 and the switching mirror 262. That is, the first aperture 224 is disposed between a first concave mirror 258 and a second concave mirror 260.

Therefore, the infrared light emitted from the light source 212 becomes the infrared light as an interference light at the interferometer 240, and reaches the first aperture 224 disposed between the first concave mirror 258 and the second concave mirror 260. Then, the shape of the infrared light which became the interference light is changed to the shape shown in FIG. 2 (b) by the first aperture 224. The infrared light transmitted through the sample 216 (or the infrared light reflected by the sample 216) is reflected by the switching mirror 262 to the irradiation path A (or B), guided toward the sample 216 by an irradiating mirror 222A (or 222B), reflected toward an irradiating Cassegrain mirror 226 (or a focusing Cassegrain mirror 228) by a transmitted light guiding mirror 264 (or a reflected light guiding mirror 266), and irradiated to the sample 216 by the irradiating Cassegrain mirror 226 (or the focusing Cassegrain mirror 228) while maintaining the shape as the beam-spot formed by the first aperture 224.

Then, the infrared light transmitted through (or reflected by the sample 216) is focused by the focusing Cassegrain mirror 228, and transmits through the reflected light guiding mirror 266. Only the infrared light which is in focus at the second aperture 230 having corresponding positions and sizes of the holes of the first aperture 224 passes through the reflected light guiding mirror 266. The infrared light is then reflected toward a focusing mirror 232 by a first plane mirror 268 and a second plane mirror 270, and guided to a MCT detector 220 by the focusing mirror 232 to perform a good measurement with less crosstalk.

As described above, the first aperture 224 is not disposed in the irradiation paths A and B, but is disposed between the interferometer 240 and the switching mirror 262, that is, between the first concave mirror 258 and the second concave mirror 260. Accordingly, effects similar to the second embodiment can be obtained.

Fourth Embodiment

Next, an infrared microscope according to the fourth embodiment of the present invention is described with reference to the figures. Configurations in common with the infrared microscope 110 of the second embodiment shown in FIG. 5 are represented with reference numbers of which 200 are added respectively.

Figure 7:
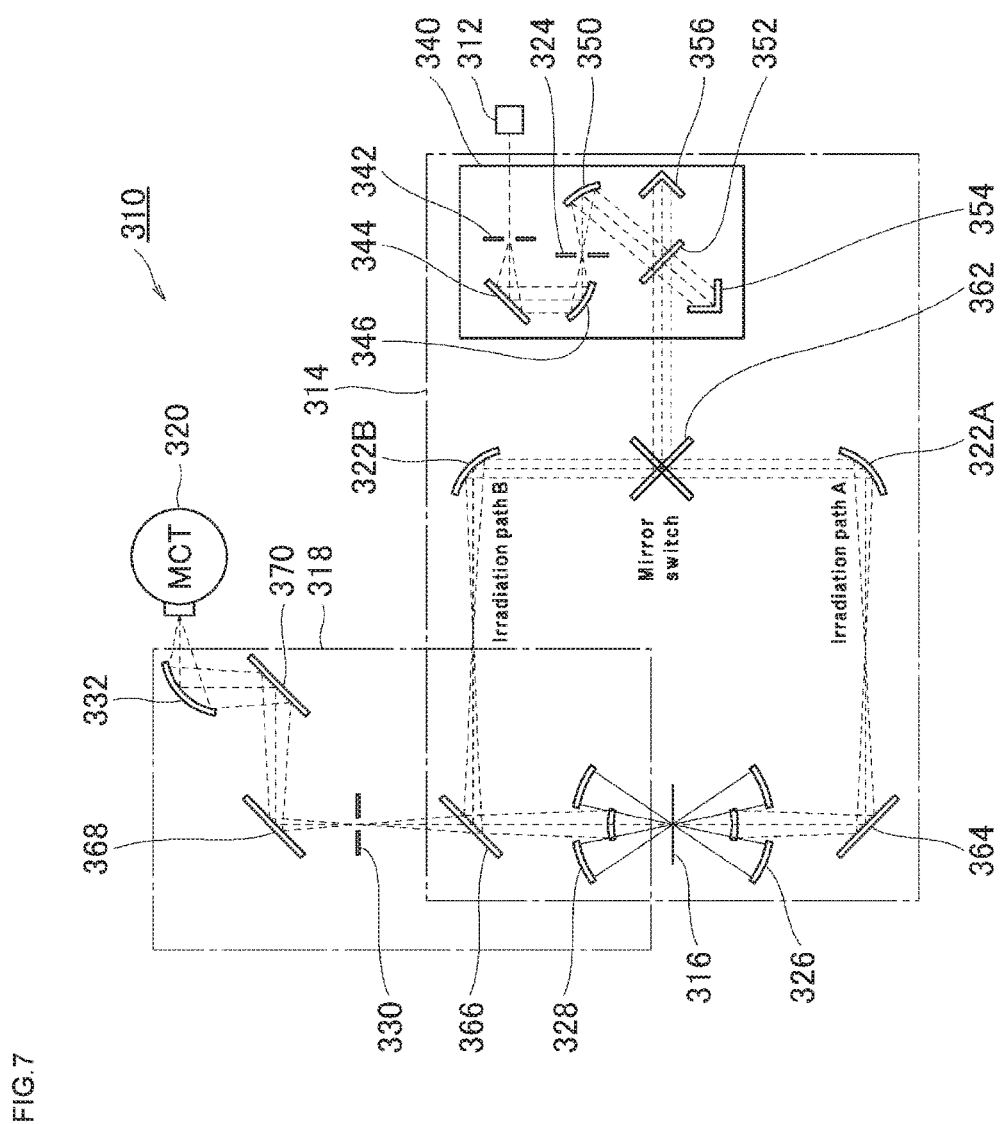
FIG. 7 shows a schematic configuration of a fourth embodiment of the infrared microscope according to the present invention.

FIG. 7 is a schematic diagram of the infrared microscope according to the fourth embodiment of the present invention. Basic configuration of the infrared microscope 310 shown in FIG. 7 is the same as the infrared microscope 110 shown in FIG. 5. A characteristic feature of the present embodiment is that a resolution determining slit for determining wavenumber resolution of an interferometer 340 act as a first aperture 324 and performs aperture function. Therefore, in the present embodiment, the first aperture is not provided independently like the other embodiments. Thus, similar effect can be obtained in a configuration simpler than the second and third embodiments (FIGS. 5 and 6).

As described above, according to the infrared microscope of the present invention, the first aperture, which has at least one or more holes and can be selected in accordance with measurement, is provided between the light source and the sample, and the second aperture corresponding to the first aperture is provided between the sample and the detector, so that confocal effect at a plurality of points can be obtained simultaneously, and measurement with good accuracy and less crosstalk becomes possible.

In addition, by providing the irradiation paths A and B in the infrared light irradiating optical system, disposing the first apertures at both of the irradiation paths respectively, and providing the second aperture in the infrared light focusing optical system, a good measurement with less crosstalk can be performed, and an infrared microscope capable of measurement by transmission and reflection can be obtained.

Further, the first aperture is provided between the sample and the switching mirror, so that the first aperture does not have to be provided in two. Thus, a good measurement with less crosstalk can be performed, and an infrared microscope capable of measurement by transmission and reflection can be obtained.

DESCRIPTION OF REFERENCE NUMBERS 10, 110, 210, 310 Infrared microscope
12, 112, 212, 312 Light source
14, 114, 214, 314 Infrared light irradiating optical system
16, 116, 216, 316 Sample
18, 118, 218, 318 Infrared light focusing optical system
20, 120, 220, 320 MCT detector
22, 122A, 222A, 322A Irradiating mirror
122B, 222B, 322B Irradiating mirror
24, 124A, 124B, 224, 324 First aperture
26, 126, 226, 326 Irradiating Cassegrain mirror
28, 128, 228, 328 Focusing Cassegrain mirror
30, 130, 230, 330 Second aperture
32, 132, 232, 332 Focusing mirror
140, 240, 340 Interferometer
142, 242, 342 Interferometer slit
144, 244, 344 First interferometer mirror
146, 246, 346 Second interferometer mirror
148, 248 Resolution determining slit
150, 250, 350 Third interferometer mirror
152, 252, 352 Semi-transparent mirror
154, 254, 354 Fixed mirror
156, 256, 356 Moving mirror
258 First concave face mirror
260 Second concave face mirror
162, 262, 362 Switching mirror
164, 264, 364 Transmitted light guiding mirror
166, 266, 366 Reflected light guiding mirror
168, 268, 368 First plane mirror
170, 270, 370 Second plane mirror

What is claimed is:
1. An infrared microscope comprising:
a light source for irradiating an infrared light, an infrared light irradiating unit for irradiating the infrared light to a sample, an infrared light focusing unit for focusing the infrared light transmitted through or reflected by the sample, and a detector for detecting the focused infrared light,
wherein the infrared light irradiating unit comprises a first aperture, and the first aperture is disposed at a position where the infrared light from the light source passes to be irradiated to the sample;
the infrared light focusing unit comprises a second aperture, and the second aperture is disposed at an imaging point of the infrared light at the first aperture;
the first aperture has a plurality of holes;
the holes are disposed with intervals which correspond to an arrangement of light-receiving elements disposed in the detector, so that the detector can detect the infrared light as a detecting light; and the second aperture has holes having the same size and arrangement as the first aperture.

2. The infrared microscope according to claim 1, wherein the first and the second aperture are provided in pluralities having different number of holes or different arrangements, and are selected in accordance with a wavelength of the infrared light.

3. The infrared microscope according to claim 1, wherein the holes of the first and the second aperture are disposed with regular intervals in one direction.

4. The infrared microscope according to claim 2, wherein the holes of the first and the second aperture are disposed with regular intervals in one direction.

5. The infrared microscope according to claim 1, wherein the holes of the first and the second aperture are two-dimensionally disposed with regular intervals in a first and a second arrangement direction.

6. The infrared microscope according to claim 2, wherein the holes of the first and the second aperture are two-dimensionally disposed with regular intervals in a first and a second arrangement direction.

7. The infrared microscope according to claim 3, wherein the holes of the first and the second aperture are two-dimensionally disposed with regular intervals in a first and a second arrangement direction.

8. The infrared microscope according to claim 4, wherein the holes of the first and the second aperture are two-dimensionally disposed with regular intervals in a first and a second arrangement direction.

9. The infrared microscope according to claim 1, wherein the holes of the first and the second aperture are disposed with irregular intervals in one direction.

10. The infrared microscope according to claim 2, wherein the holes of the first and the second aperture are disposed with irregular intervals in one direction.

11. The infrared microscope according to claim 9, wherein the holes of the first and the second aperture are two-dimensionally disposed with irregular intervals in a first and the second arrangement direction.

12. The infrared microscope according to claim 10, wherein the holes of the first and the second aperture are two-dimensionally disposed with irregular intervals in a first and the second arrangement direction.

13. The infrared microscope according to claim 1, wherein both or either one of the infrared light irradiating unit and the infrared light focusing unit for focusing the infrared light transmitted through the sample comprises a Cassegrain mirror.

14. The infrared microscope according to claim 8, wherein both or either one of the infrared light irradiating unit and the infrared light focusing unit for focusing the infrared light transmitted through the sample comprises a Cassegrain mirror.

15. The infrared microscope according to claim 1, wherein the infrared light irradiating unit and the infrared light focusing unit for focusing the infrared light transmitted through the sample uses the same Cassegrain mirror.

16. The infrared microscope according to claim 2, wherein the detector is a MCT detector, and the aperture is switched in accordance with the arrangement of the light-receiving elements in the MCT detector and the wavelength of the infrared light.

17. The infrared microscope according to claim 8, wherein the detector is a MCT detector, and the aperture is switched in accordance with the arrangement of the light-receiving elements in the MCT detector and the wavelength of the infrared light.

18. The infrared microscope according to claim 1, wherein the infrared light irradiating unit comprises an interferometer for producing an interference wave from the infrared light irradiated form the light source in accordance with scanning of a moving mirror, and an analyzer for analyzing the interference wave of the infrared light detected by the detector is provided.

19. The infrared microscope according to claim 17, wherein the infrared light irradiating unit comprises an interferometer for producing an interference wave from the infrared light irradiated form the light source in accordance with scanning of a moving mirror, and an analyzer for analyzing the interference wave of the infrared light detected by the detector is provided.

20. The infrared microscope according to claim 18, wherein the first aperture is included in the interferometer.

21. The infrared microscope according to claim 1, wherein the infrared light irradiating unit comprises a first irradiation path for measurement by transmission and a second irradiation path for measurement by reflection, and both of the first and the second irradiation path comprise the first aperture.

22. The infrared microscope according to claim 18, wherein the infrared light irradiating unit comprises a first irradiation path for measurement by transmission and a second irradiation path for measurement by reflection, and both of the first and the second irradiation path comprise the first aperture.

23. The infrared microscope according to claim 20, wherein the infrared light irradiating unit comprises a first irradiation path for measurement by transmission and a second irradiation path for measurement by reflection, and both of the first and the second irradiation path comprise the first aperture.

24. The infrared microscope according to claim 1, wherein the wavelength of the infrared light is 2 μm or more.

* * * * *